(12) United States Patent
Oosake et al.

(10) Patent No.: US 11,704,794 B2
(45) Date of Patent: Jul. 18, 2023

(54) FILING DEVICE, FILING METHOD, AND PROGRAM (71) Applicant: FUJIFILM Corporation, Tokyo (JP)

(72) Inventors: Masaaki Oosake, Kanagawa (JP); Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 164 days.

(21) Appl. No.: 16/941,552

(22) Filed: Jul. 29, 2020

(65) Prior Publication Data

US 2021/0042914 A1 Feb. 11, 2021

(30) Foreign Application Priority Data

Aug. 9, 2019 (JP) .................................. 2019-147380

(51) Int. Cl.
*G06T 7/00* (2017.01)
*G06T 7/20* (2017.01)
*G16H 30/20* (2018.01)
*G16H 30/40* (2018.01)

(52) U.S. Cl.
CPC .............. *G06T 7/0012* (2013.01); *G06T 7/20* (2013.01); *G16H 30/20* (2018.01); *G16H 30/40* (2018.01); *G06T 2207/10068* (2013.01); *G06T 2207/30096* (2013.01)

(58) Field of Classification Search
CPC ..................... G06T 7/0012; G06T 7/20; G06T 2207/10016; G06T 2207/10068; G06T 2207/30096; G16H 30/20; G16H 30/40; G16H 50/20
See application file for complete search history.

(56) References Cited

U.S. PATENT DOCUMENTS

| 8,315,503 | B2 | 11/2012 | Shimazaki et al. |
| 10,491,778 | B2 * | 11/2019 | De Mers ................. G06T 11/60 |
| 10,778,916 | B2 * | 9/2020 | Jahagirdar .............. G06T 19/00 |

(Continued)

FOREIGN PATENT DOCUMENTS

| JP | 2005044004 | 2/2005 |
| JP | 2006135394 | 5/2006 |

(Continued)

OTHER PUBLICATIONS

"Office Action of Japan Counterpart Application" with English translation thereof, dated Jul. 19, 2022, p. 1-p. 6.

(Continued)

*Primary Examiner* — Amandeep Saini
*Assistant Examiner* — Julius Chai
(74) *Attorney, Agent, or Firm* — JCIPRNET (57) ABSTRACT

There is provided a filing device, a filing method, and a program that cause a still image and a motion image to be associated with each other, which are captured without being associated with each other.

The problem is solved through a filing device including an acquisition unit that acquires at least one still image and at least one motion image, a still image analysis unit that analyzes a pixel value of the still image and extracts still image information, a motion image analysis unit that analyzes a pixel value of the motion image and extracts motion image information, and an associating unit that associates the still image with the motion image by comparing the still image information with the motion image information.

9 Claims, 7 Drawing Sheets

(56) References Cited

U.S. PATENT DOCUMENTS

| | | | |
|---|---|---|---|
| 10,867,217 B1* | 12/2020 | Madden | G06V 10/987 |
| 10,956,492 B2* | 3/2021 | Barral | G06F 16/739 |
| 2009/0125136 A1 | 5/2009 | Akiyama | |
| 2009/0303316 A1* | 12/2009 | Iwasaki | A61B 1/0004 |
| | | | 348/E7.085 |
| 2011/0150420 A1* | 6/2011 | Cordonnier | G16H 30/40 |
| | | | 386/E9.011 |
| 2012/0078045 A1 | 3/2012 | Sasaki et al. | |
| 2015/0272429 A1* | 10/2015 | Shigeta | A61B 1/0002 |
| | | | 348/65 |
| 2017/0118539 A1* | 4/2017 | Lokshin | G11B 27/28 |
| 2017/0303767 A1* | 10/2017 | Fukuda | A61B 1/0002 |
| 2018/0322949 A1* | 11/2018 | Mohr | G16H 30/20 |

FOREIGN PATENT DOCUMENTS

| | | |
|---|---|---|
| JP | 2007296079 | 11/2007 |
| JP | 2007319478 | 12/2007 |
| JP | 2009117973 | 5/2009 |
| JP | 2012134864 | 7/2012 |
| WO | 2009136507 | 11/2009 |

OTHER PUBLICATIONS

"Notice of Reasons for Refusal of Japan Counterpart Application", dated Dec. 19, 2022, with English translation thereof, p. 1-p. 10.

* cited by examiner

FILING DEVICE, FILING METHOD, AND PROGRAM

CROSS-REFERENCE TO RELATED APPLICATIONS

The present application claims priority under 35 U.S.C § 119 to Japanese Patent Application No. 2019-147380 filed on Aug. 9, 2019. The above application is hereby expressly incorporated by reference, in its entirety, into the present application.

BACKGROUND OF THE INVENTION

1. Field of the Invention

The present invention relates to a filing device, a filing method, and a program, and particularly relates to a technique of associating a still image with a motion image.

2. Description of the Related Art

In endoscopy, there is known a computer aided diagnosis (CAD) technique that analyzes an endoscope image with a computer to support diagnosis.

Deep learning is useful in developing CAD related to endoscopy. Since a large amount of learning data is necessary in order to perform deep learning, saving endoscopy as a motion image to set as learning data is considered. In addition, a still image is captured during endoscopy in some cases. In a case where a saving target such as CCAM, a lesion, and inflammation is found in the endoscopy, a surgeon captures a still image including the saving target through scope operation.

In a case where a learning target such as CCAM, a lesion, and inflammation is found in a motion image, which is learning data, it is necessary to play the motion image and check a part where the learning target is imaged. In this case, in a case where the learning target is imaged in a still image associated with the motion image, the part where the learning target is imaged can be identified based on information on the still image without playing the motion image.

An information processing apparatus that assigns management information during motion image capturing to a still image in a case where the still image is captured during motion image capturing is disclosed in JP2012-134864A.

SUMMARY OF THE INVENTION

However, there is a problem that it is necessary to manually check the still image and the motion image and associate the still image and the motion image with each other, which are not associated with each other at the time of imaging.

The present invention is devised in view of such circumstances, and an object thereof is to provide a filing device, a filing method, and a program that cause a still image and a motion image to be associated with each other, which are captured without being associated with each other.

According to an aspect of the invention, in order to achieve the object, there is provided a filing device comprising an acquisition unit that acquires at least one still image and at least one motion image, a still image analysis unit that analyzes a pixel value of the still image and extracts still image information, a motion image analysis unit that analyzes a pixel value of the motion image and extracts motion image information, and an associating unit that associates the still image with the motion image by comparing the still image information with the motion image information.

According to the aspect, the still image and the motion image, which are captured without being associated with each other, can be associated with each other.

It is preferable that the acquisition unit acquires the still image recorded by a first device and the motion image recorded by a second device different from the first device. Accordingly, even in a case where the still image and the motion image are recorded by the different devices, the still image and the motion image can be associated with each other.

It is preferable that the still image information and the motion image information include imaging date and time information. Accordingly, the still image and the motion image can be appropriately associated with each other.

It is preferable that the acquisition unit acquires a still image group, which is a group of a plurality of the still images stored within a certain period. Accordingly, the still image and the motion image can be appropriately associated with each other.

It is preferable that the associating unit associates a first motion image with a first still image group imaged when capturing the first motion image. Accordingly, the still image and the motion image can be appropriately associated with each other.

It is preferable that the still image information includes earliest imaging date and time and latest imaging date and time of the still image group. It is preferable that the motion image information includes imaging starting date and time and imaging finishing date and time of the motion image. It is preferable that in a case where earliest imaging date and time of the first still image group are later than imaging starting date and time of the first motion image and latest imaging date and time of the first still image group are earlier than imaging finishing date and time of the first motion image, the associating unit associates the first motion image with the first still image group. Accordingly, the still image and the motion image can be appropriately associated with each other.

It is preferable that the acquisition unit acquires the still image and the motion image that are endoscope images obtained by imaging a patient in an endoscope system. Accordingly, the still image and the motion image can be appropriately associated with each other.

It is preferable that the still image information and the motion image information include information on a scope of the endoscope system. Accordingly, the still image and the motion image can be appropriately associated with each other.

It is preferable that the still image information and the motion image information include information on the patient and an examination. Accordingly, the still image and the motion image can be appropriately associated with each other.

It is preferable that the still image information and the motion image information include information on a facility where the endoscope system is provided. Accordingly, the still image and the motion image can be appropriately associated with each other.

According to another aspect of the invention, in order to achieve the object, there is provided a filing method comprising a still image analyzing step of analyzing a pixel value of a still image and extracting still image information, a motion image analyzing step of analyzing a pixel value of a motion image and extracting motion image information, an acquiring step of acquiring at least one still image and at least one motion image, and an associating step of associating the at least one still image with the at least one motion image by comparing the still image information with the motion image information.

According to the aspect, the still image and the motion image, which are captured without being associated with each other, can be associated with each other.

A program for causing a computer to execute the filing method is also included in the aspect.

According to the present invention, the still image and the motion image, which are captured without being associated with each other, can be associated with each other.

DESCRIPTION OF THE PREFERRED EMBODIMENTS

Hereinafter, preferable embodiments of the present invention will be described in detail with reference to the accompanying drawings.

Configuration of Filing Device

A filing device 10 according to an embodiment of the present invention is a device that associates a still image with a motion image in order to collect learning data used in learning of a learning model. The filing device 10 is realized by a general-purpose computer, for example, a personal computer, a microcomputer, or the like.

Figure 1:
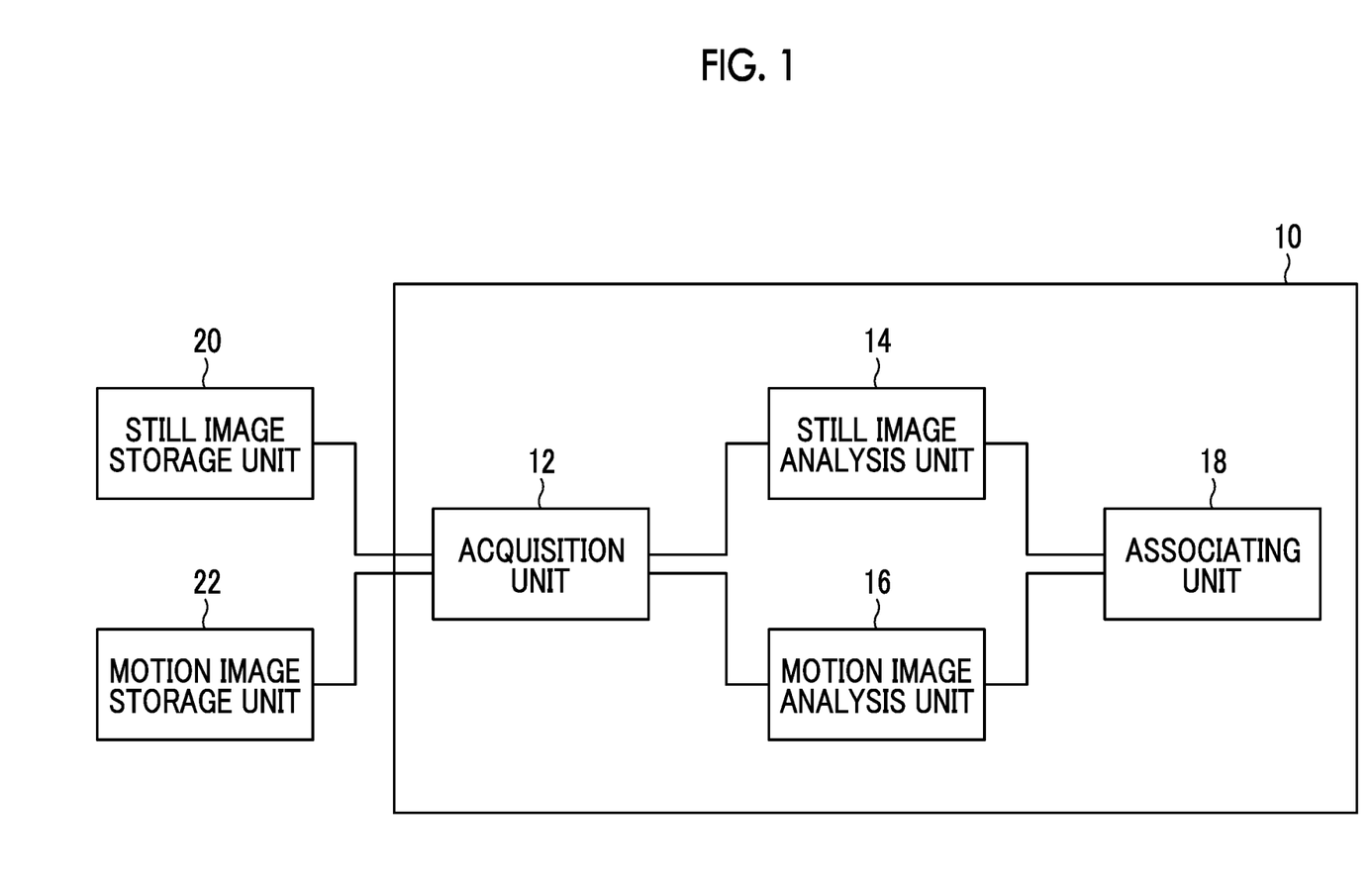
FIG. 1 is a block diagram showing an example of a hardware configuration of a filing device.

FIG. 1 is a block diagram showing an example of a hardware configuration of the filing device 10. The filing device 10 comprises an acquisition unit 12, a still image analysis unit 14, a motion image analysis unit 16, and an associating unit 18.

The filing device 10 is connected to a still image storage unit 20 and a motion image storage unit 22 so as to be capable of communicating in a wired or wireless manner. The still image storage unit 20 is, for example, a large-capacity storage device provided in an endoscope system 100 (refer to FIG. 7). The still image storage unit 20 stores a plurality of still images recorded by an endoscope processor device 112 (an example of a first device), the still images being endoscope images obtained by imaging a patient through the endoscope system 100.

Figure 7:
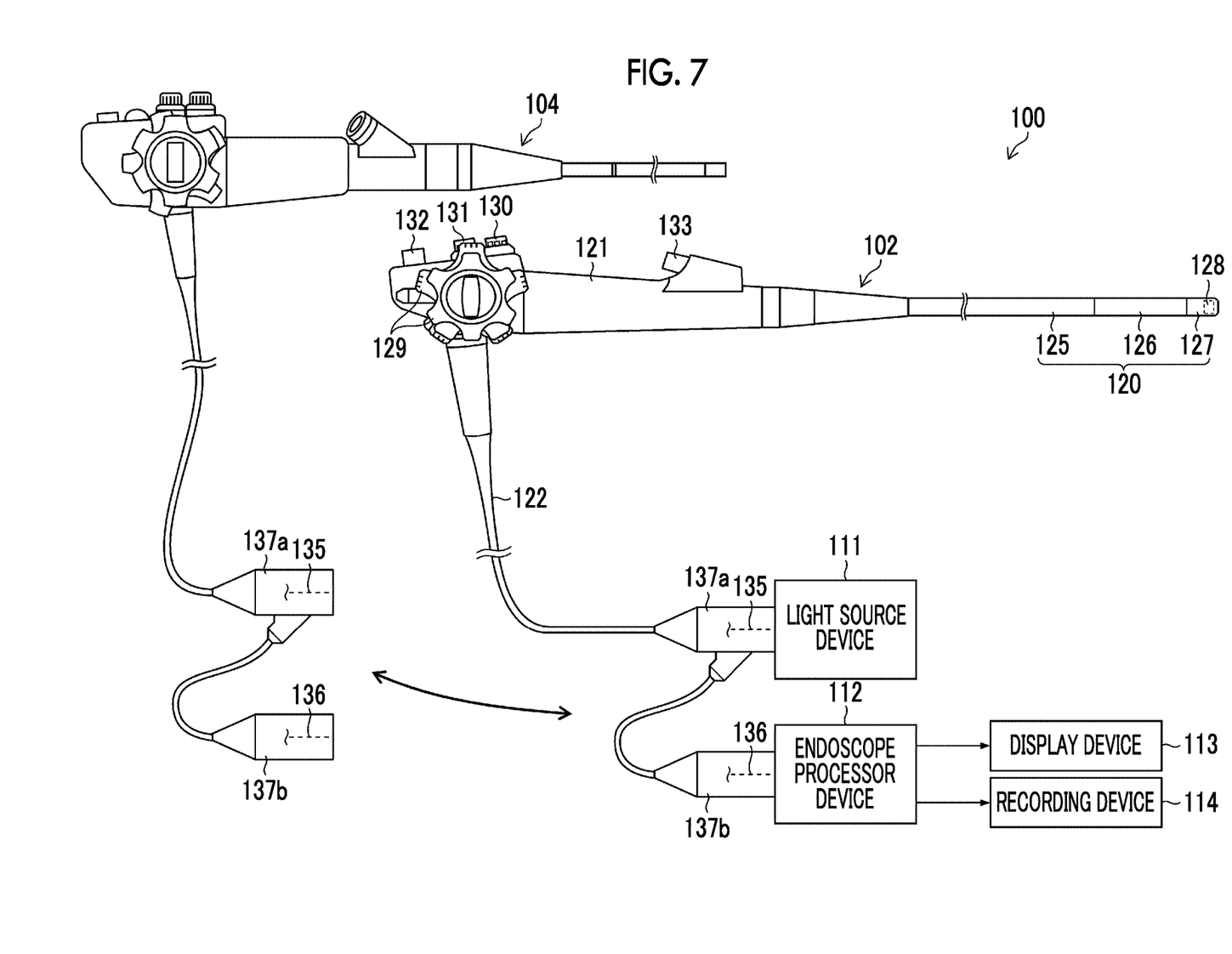
FIG. 7 is a schematic view illustrating an overall configuration of an endoscope system.

The motion image storage unit 22 is, for example, a large-capacity storage device provided in a recording device 114 (refer to FIG. 7). The motion image storage unit 22 stores a plurality of motion images recorded by the recording device 114 (an example of a second device), the motion images being endoscope images obtained by imaging a patient through the endoscope system 100.

The acquisition unit 12 acquires at least one still image from the still image storage unit 20 and acquires at least one motion image from the motion image storage unit 22.

The still image analysis unit 14 analyzes a pixel value of the still image acquired by the acquisition unit 12 and extracts still image information. The still image analysis unit 14 may comprise a text recognition unit (not shown) that recognizes text through optical character reader (OCR) processing and converts the text into text data.

The motion image analysis unit 16 analyzes a pixel value of the motion image acquired by the acquisition unit 12 and extracts motion image information. The motion image analysis unit 16 may comprise a text recognition unit (not shown) that recognizes text through OCR processing and converts the text into text data.

The associating unit 18 associates the still image and the motion image with each other, which are acquired by the acquisition unit 12, by comparing the still image information extracted by the still image analysis unit 14 with the motion image information extracted by the motion image analysis unit 16.

The filing device 10 may comprise an output unit that outputs information associated by the associating unit 18 to the outside of the filing device 10 or a storage unit that stores information associated by the associating unit 18 inside the filing device 10.

Endoscope Image: First Embodiment

Figure 2:
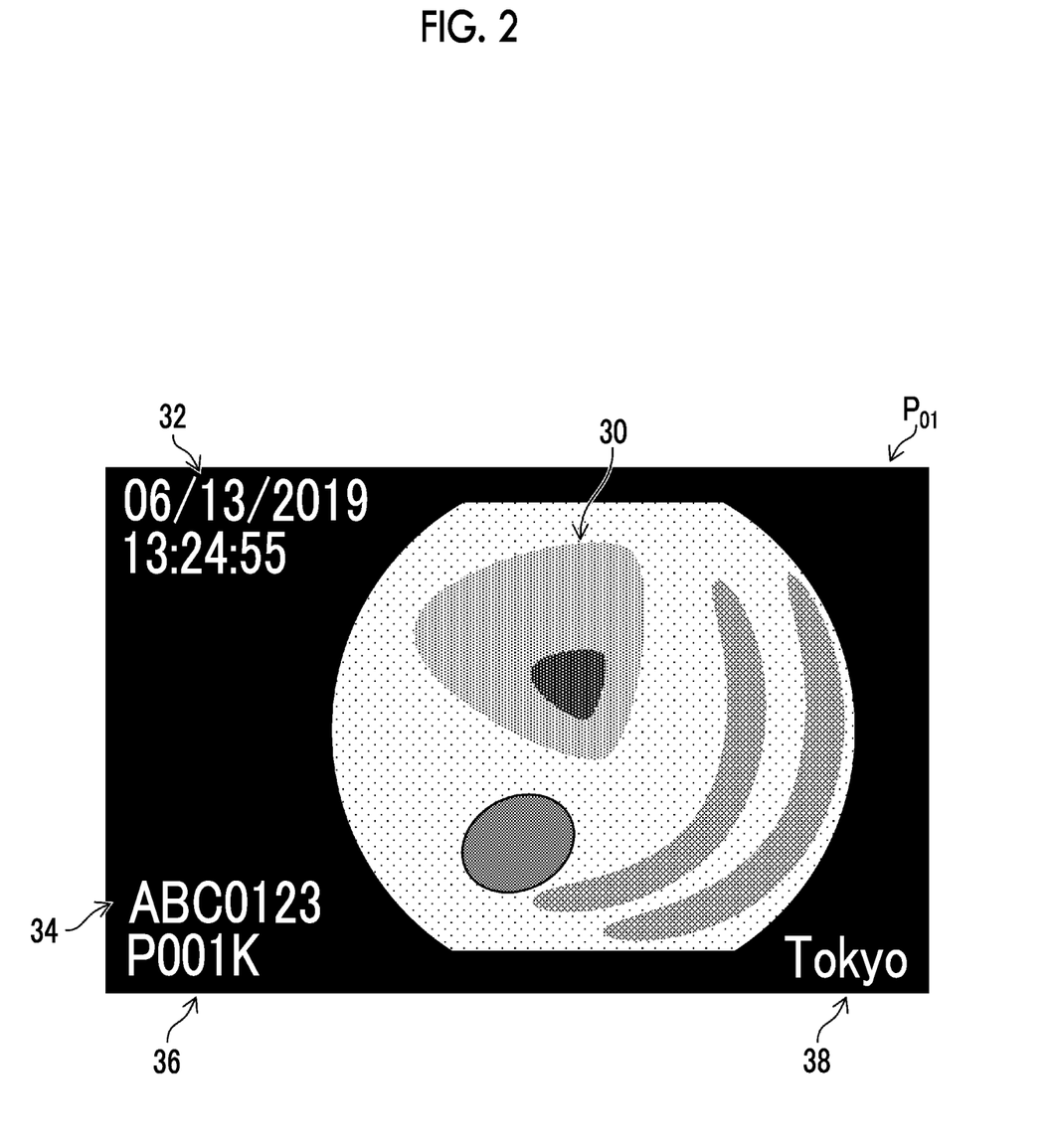
FIG. 2 is a view illustrating an example of a still image stored in a still image storage unit.

FIG. 2 is a view illustrating an example of a still image Poi stored in the still image storage unit 20. In addition to a subject image 30 in which an inside of a body of a patient is imaged, date and time information 32, a scope ID 34, a patient/examination ID 36, and facility information 38 are imaged in the still image Poi. The ID is an abbreviation of identification.

The date and time information 32 (an example of imaging date and time information) is information on time, day, month, and year when the still image Poi is captured. In the example illustrated in FIG. 2, the date and time information 32 is "2019/6/13 13:24:55", which indicates that imaging date and time is "13:24:55, Jun. 13, 2019".

The scope ID 34 is information for identifying the type of an endoscope scope 102 (refer to FIG. 7) of the endoscope system 100 that has captured the still image Poi. In the example illustrated in FIG. 2, the scope ID 34 is "ABC0123".

The patient/examination ID 36 is information for identifying a patient and an examination of the still image Poi. In the example illustrated in FIG. 2, the patient/examination ID 36 is "P001K".

The facility information 38 is information for identifying a facility where the still image $P_{01}$ is captured, and is equivalent to information for identifying a facility where the endoscope system 100 is provided. In the example illustrated in FIG. 2, the facility information 38 is "Tokyo".

As described above, the subject image 30, the date and time information 32, the scope ID 34, the patient/examination ID 36, and the facility information 38 are text that is imaged in the image. Therefore, the still image Poi has information on the subject image 30, the date and time information 32, the scope ID 34, the patient/examination ID 36, and the facility information 38 as a pixel value in the image.

Although the still image has been described herein, the subject image 30, the date and time information 32, the scope ID 34, the patient/examination ID 36, and the facility information 38 are also imaged in each frame image configuring a motion image, the motion image being stored in the motion image storage unit 22. That is, also the motion image has information on the subject image 30, the date and time information 32, the scope ID 34, the patient/examination ID 36, and the facility information 38 as a pixel value in the image.

The disposition of the subject image 30, the date and time information 32, the scope ID 34, the patient/examination ID 36, and the facility information 38 is not limited to the example of FIG. 2, and the information may be imaged in the image. In addition, the still image and the motion image may have at least the subject image 30, and may not have the date and time information 32, the scope ID 34, the patient/examination ID 36, and the facility information 38.

Imaging Timing

Figure 3:
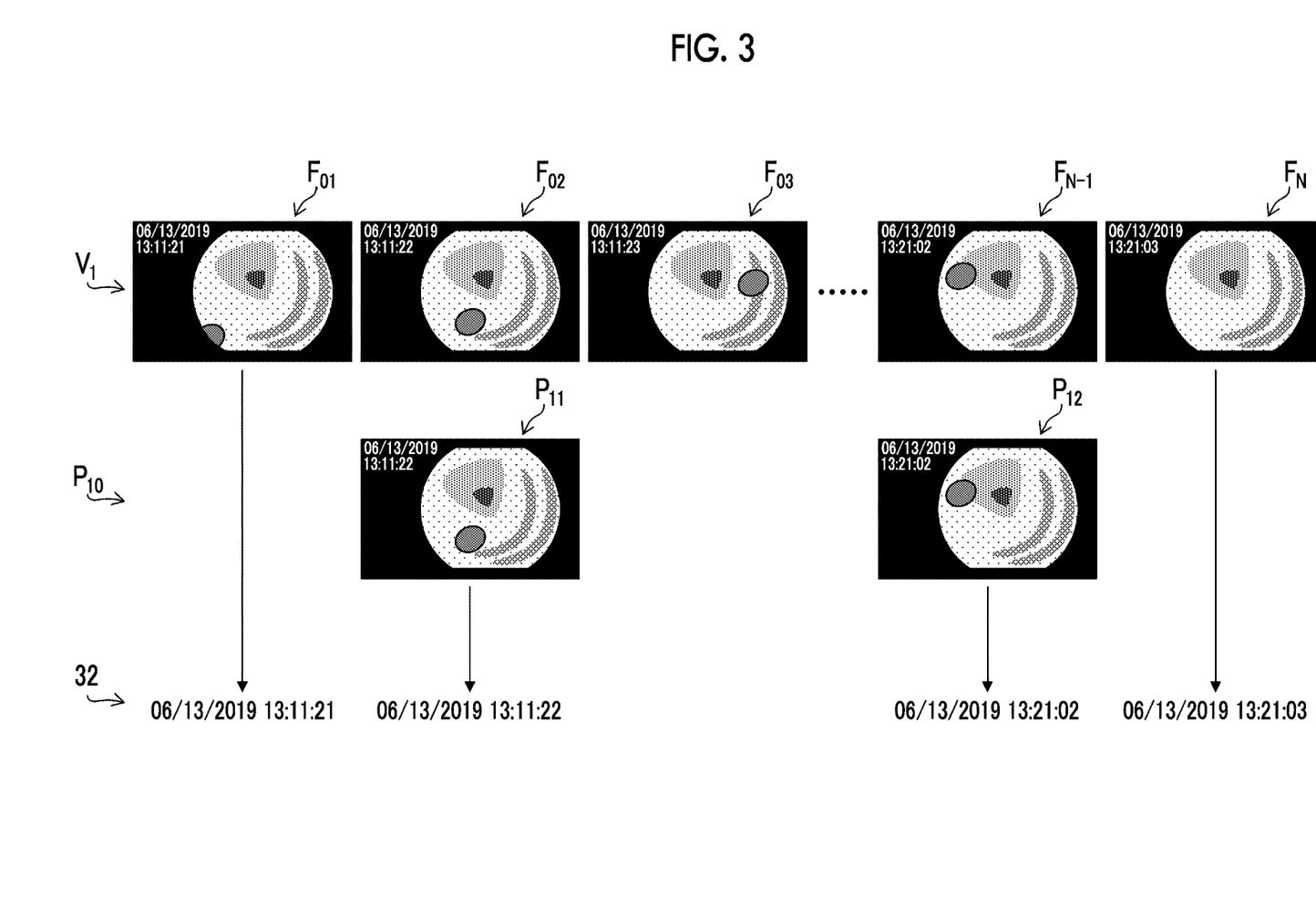
FIG. 3 is a view for describing imaging timings of a motion image and a still image.

FIG. 3 is a view for describing imaging timings of a motion image and a still image. A motion image $V_1$ illustrated in FIG. 3 is configured by N frame images captured from imaging starting date and time to imaging finishing date and time. In addition, a still image group $P_{10}$ illustrated in FIG. 3 is configured by a plurality of still images which are stored and associated with each other within a certain period. Herein, the still image group $P_{10}$ is a group of images captured during a motion image $V_1$ imaging period.

Time elapses from left to right in FIG. 3. Each of frame images $F_{01}$, $F_{02}$, $F_{03}$, . . . , $F_{N-1}$, and $F_N$ of the motion image $V_1$ is shown in an upper part of FIG. 3. Two still images $P_{11}$ and $P_{12}$ configuring the still image group $P_{10}$ is shown in a middle part of FIG. 3. The date and time information 32 of each of the frame image $F_{01}$, the still image $P_{11}$, the still image $P_{12}$, and the frame image $F_N$ is shown in a lower part of FIG. 3.

Imaging starting date and time of the motion image $V_1$ is "13:11:21, Jun. 13, 2019" as can be seen from the date and time information 32 of the first frame image $F_{01}$ of the motion image $V_1$. In addition, imaging finishing date and time of the motion image $V_1$ is "13:21:03, Jun. 13, 2019" as can be seen from the date and time information 32 of the last frame image $F_N$ of the motion image $V_1$.

Imaging date and time of the still image $P_{11}$ is "13:11:22, Jun. 13, 2019" as can be seen from the date and time information 32 of the still image $P_{11}$. In addition, imaging date and time of the still image $P_{12}$ is "13:21:02, Jun. 13, 2019" as can be seen from the date and time information 32 of the still image $P_{12}$.

As described above, the still image group $P_{10}$, which is imaged when capturing the motion image $V_1$, is imaged from the imaging starting date and time to the imaging finishing date and time of the motion image $V_1$. That is, the motion image $V_1$ and the still image group $P_{10}$ imaged when capturing the motion image $V_1$ have a relationship in which the earliest imaging date and time of the still image group $P_{10}$ are later than imaging starting date and time of the motion image $V_1$ and the latest imaging date and time of the still image group $P_{10}$ are earlier than the imaging finishing date and time of the motion image $V_1$.

The still image group $P_{10}$ and the motion image $V_1$ which are captured in such a manner are stored in the still image storage unit 20 and the motion image storage unit 22, respectively, without being associated with each other.

Filing Method

Figure 4:
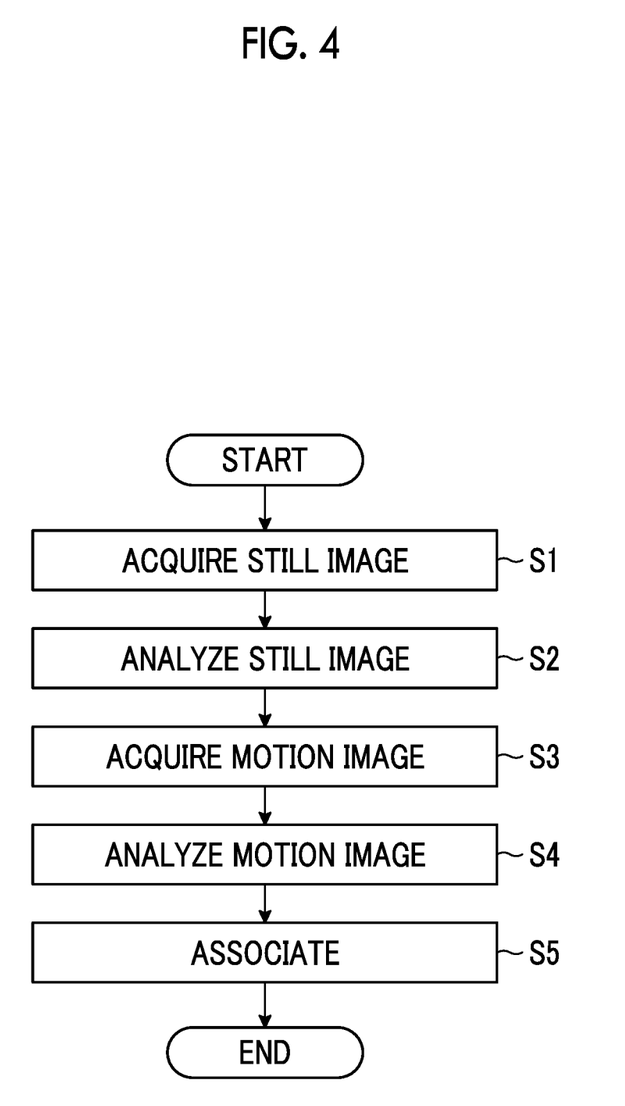
FIG. 4 is a flowchart showing an example of a filing method.

FIG. 4 is a flowchart showing an example of a filing method for the filing device 10. The filing device 10 executes the filing method by executing a program stored in a hard disk device (not shown) or the like. Herein, an example in which a motion image is associated with a still image group imaged when capturing the motion image will be described.

As shown in FIG. 4, the filing method comprises a still image acquiring step (Step S1), a still image analyzing step (Step S2), a motion image acquiring step (Step S3), a motion image analyzing step (Step S4), and an associating step (Step S5).

First, in Step S1, the acquisition unit 12 acquires at least one still image from the still image storage unit 20. For example, the acquisition unit 12 acquires a still image group that is a group of a plurality of still images which are stored and associated with each other within a certain period in the still image storage unit 20.

Figure 5:
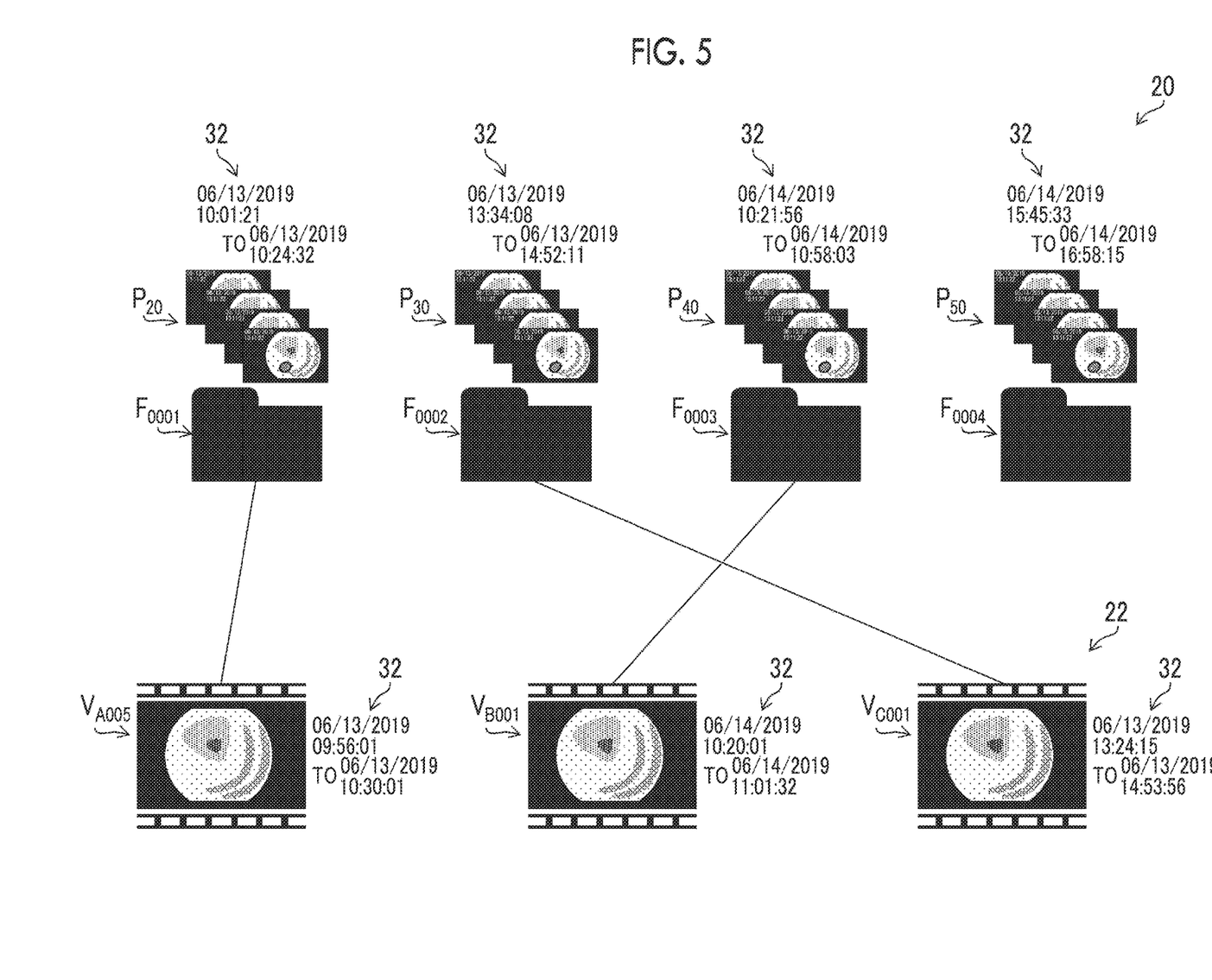
FIG. 5 is a view illustrating an example of the motion image and the still image.

FIG. 5 is a view illustrating examples of a still image stored in the still image storage unit 20 and a motion image stored in the motion image storage unit 22. As illustrated in FIG. 5, still image groups $P_{20}$, $P_{30}$, $P_{40}$, and $P_{50}$ that consist of a plurality of still images are respectively stored in folders $F_{0001}$, $F_{0002}$, $F_{0003}$, and $F_{0004}$ of the still image storage unit 20. Herein, the acquisition unit 12 acquires the still image groups $P_{20}$, $P_{30}$, $P_{40}$, and $P_{50}$. Whether the still image groups $P_{20}$, $P_{30}$, $P_{40}$, and $P_{50}$ are a plurality of still images stored in the still image storage unit 20 within a certain period can be determined based on metadata of each still image.

Next, in Step S2, the still image analysis unit 14 analyzes a pixel value of the still image acquired in Step S1 and extracts still image information. Herein, the still image information refers to the earliest imaging date and time and the latest imaging date and time of each still image group. That is, the still image analysis unit 14 analyzes a pixel value of the date and time information 32 of each of the still images in the still image groups $P_{20}$, $P_{30}$, $P_{40}$, and $P_{50}$, and extracts the still image information.

As can be seen from the date and time information 32 of each of the still image groups $P_{20}$, $P_{30}$, $P_{40}$, and $P_{50}$ illustrated in FIG. 5, the earliest imaging date and time of the still image group $P_{20}$ is "10:01:21, Jun. 13, 2019", and the latest imaging date and time is "10:24:32, Jun. 13, 2019". In addition, the earliest imaging date and time of the still image group $P_{30}$ is "13:34:08, Jun. 13, 2019", and the latest imaging date and time is "14:52:11, Jun. 13, 2019". Similarly, the earliest imaging date and time of the still image group $P_{40}$ is "10:21:56, Jun. 14, 2019", and the latest imaging date and time is "10:58:03, Jun. 14, 2019". Further, the earliest imaging date and time of the still image group $P_{50}$ is "15:45:33, Jun. 14, 2019", and the latest imaging date and time is "16:58:15, Jun. 14, 2019".

Next, in Step S3, the acquisition unit 12 acquires at least one motion image from the motion image storage unit 22.

As illustrated in FIG. 5, motion images $V_{A005}$, $V_{B001}$, and $V_{C001}$ are stored in the motion image storage unit 22. Herein, the acquisition unit 12 acquires the motion images $V_{A005}$, $V_{B001}$, and $V_{C001}$.

Next, in Step S4, the motion image analysis unit 16 analyzes a pixel value of the motion image acquired in Step S3, and extracts motion image information. Herein, the motion image information refers to imaging starting date and time and imaging finishing date and time. That is, the motion image analysis unit 16 analyzes a pixel value of the date and time information 32 of each first frame image and a pixel value of the date and time information 32 of each last frame image of the motion images $V_{A005}$, $V_{B001}$, and $V_{C001}$, and extracts motion image information.

As can be seen from each piece of date and time information 32 illustrated in FIG. 5, imaging starting date and time of the motion image $V_{A005}$ is "09:56:01, Jun. 13, 2019", and imaging finishing date and time thereof is "10:30:01, Jun. 13, 2019". In addition, imaging starting date and time of the motion image $V_{B001}$ is "10:20:01, Jun. 14, 2019", and imaging finishing date and time thereof is "11:01:32, Jun. 14, 2019". Further, imaging starting date and time of the motion image $V_{C001}$ is "13:24:15, Jun. 13, 2019", and imaging finishing date and time thereof is "14:53:56, Jun. 13, 2019".

Lastly, in Step S5, the associating unit 18 associates the still image acquired in Step S1 with the motion image acquired in Step S3 by comparing the still image information extracted in Step S2 with the motion image information extracted in Step S4.

Herein, the associating unit 18 selects one still image group from the still image groups $P_{20}$, $P_{30}$, $P_{40}$, and $P_{50}$, and selects one motion image from the motion images $V_{A005}$, $V_{B001}$, and $V_{C001}$. Then, first determination is made as to whether or not the earliest imaging date and time of the selected still image group (an example of a first still image group) are later than imaging starting date and time of the selected motion image (an example of a first motion image).

In addition, the associating unit 18 makes second determination as to whether or not the latest imaging date and time of the selected still image group are earlier than the imaging finishing date and time of the selected motion image.

In a case where both of the first determination and the second determination are positive, the selected still image group and the selected motion image are associated with each other. In a case where one of the first determination or the second determination is negative, the selected still image group and the selected motion image are not associated with each other.

The associating unit 18 makes this determination for all combinations of the still image groups $P_{20}$, $P_{30}$, $P_{40}$, and $P_{50}$ and the motion images $V_{A005}$, $V_{B001}$, and $V_{C001}$. As a result, in the example illustrated in FIG. 5, the still image group $P_{20}$ and the motion image $V_{A005}$ are associated with each other, the still image group $P_{40}$ and the motion image $V_{B001}$ are associated with each other, and the still image group $P_{30}$ and the motion image $V_{C001}$ are associated with each other.

As described above, a motion image and a still image group imaged when capturing the motion image can be associated with each other, the still image and the motion image being a captured still image and a motion image that are not associated with each other.

Herein, the associating unit 18 associates a still image with a motion image by comparing still image information with motion image information based on the date and time information 32, but may further associate the still image with the motion image in a case where the scope ID 34, the patient/examination ID 36, and the facility information 38 are common to the still image and the motion image. In addition, the associating unit 18 may associate the still image with the motion image in a case where at least one of the scope ID 34, the patient/examination ID 36, or the facility information 38 is common to the still image and the motion image.

Second Embodiment

The filing device 10 according to a second embodiment associates a still image with a motion image based on the subject image 30.

Figure 6:
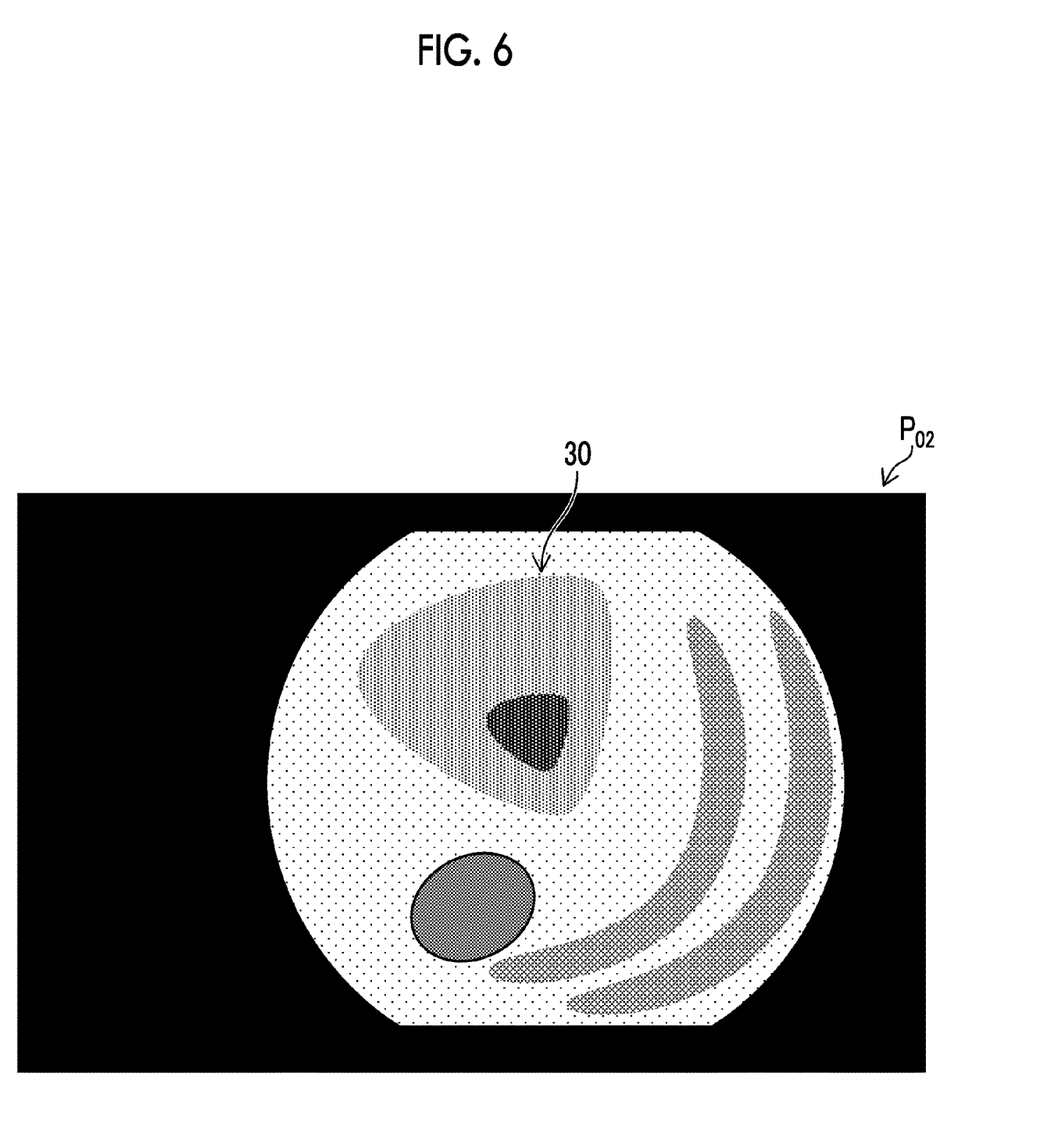
FIG. 6 is a view illustrating an example of the still image stored in the still image storage unit.

FIG. 6 is a view illustrating an example of a still image $P_{02}$ stored in the still image storage unit 20. The subject image 30 in which an inside of a body of a patient is imaged is imaged in the still image $P_{02}$, and the date and time information 32, the scope ID 34, the patient/examination ID 36, and the facility information 38 are not imaged.

In addition, the subject image 30 is also imaged in each frame configuring a motion image, the motion image being stored in the motion image storage unit 22, and the date and time information 32, the scope ID 34, the patient/examination ID 36, and the facility information 38 are not imaged.

The still image analysis unit 14 analyzes a pixel value of the subject image 30 of the still image acquired by the acquisition unit 12 and extracts still image information. Herein, the still image information is feature information on the subject image 30.

The motion image analysis unit 16 analyzes a pixel value of the subject image 30 of a frame image of a motion image acquired by the acquisition unit 12 and extracts motion image information. The motion image information is feature information on the subject image 30 just as still image information.

The associating unit 18 compares the feature information on the subject image 30, which is the still image information, with the feature information on the subject image 30, which is the motion image information, and associates the still image with the motion image in a case where the respective feature information pieces match each other or are similar to each other.

The embodiment can be applied to a case where a still image and a motion image have the date and time information 32, the scope ID 34, the patient/examination ID 36, and the facility information 38 as in the first embodiment. That is, the associating unit 18 may associate the still image with the motion image in a case where the feature information pieces of the subject images 30 of the still image and the motion image match each other or are similar to each other and the still image is captured at the time of capturing the motion image. In addition, the associating unit 18 may associate the still image with the motion image in a case where the feature information pieces of the subject images 30 of the still image and the motion image match each other or are similar to each other and at least one of the scope ID 34, the patient/examination ID 36, or the facility information 38 is common to the still image and the motion image.

Overall Configuration of Endoscope System

FIG. 7 is a schematic view illustrating an overall configuration of the endoscope system 100 according to the embodiment. The endoscope system 100 is a device that captures a still image and a motion image that are endoscope images of a part to be observed inside a body of a patient and stores the captured still image and the captured still motion image.

As illustrated in FIG. 7, the endoscope system 100 comprises the endoscope scope 102 which is an electronic endoscope, a light source device 111, the endoscope processor device 112, a display device 113, and the recording device 114.

The endoscope scope 102 is, for example, a flexible endoscope. The endoscope scope 102 has an insertion part 120 that is inserted into a body of a patient and has a distal end and a proximal end, a hand operation part 121 that is installed consecutively to a proximal end side of the insertion part 120 and performs various types of operation by being gripped by an endoscope operator (surgeon), and an universal cord 122 that is installed consecutively to the hand operation part 121.

The insertion part 120 is formed to have a small diameter and a long shape as a whole. The insertion part 120 is configured by a flexible portion 125 that has flexibility, a curving portion 126 that can be curved through operation of the hand operation part 121, and a distal end portion 127, in order from the proximal end side to a distal end side thereof.

An image pick-up portion 128 including an objective lens and an imaging element (not illustrated) is built in the distal end portion 127. The imaging element is a complementary metal oxide semiconductor (CMOS) type imaging element or a charge coupled device (CCD) type imaging element. Image light of a part to be observed is incident to an imaging surface of the imaging element via an observation window (not illustrated) opened in a distal end surface of the distal end portion 127 and the objective lens (not illustrated) disposed behind the observation window. The imaging element picks up an image of (converts into an electric signal) the image light of the part to be observed, which is incident to the imaging surface, and outputs an image pick-up signal.

The hand operation part 121 is provided with various types of operation members operated by an endoscope operator. Specifically, the hand operation part 121 is provided with two types of curving operation knobs 129 used in curving operation of the curving portion 126, an air supply and water supply button 130 for air supply and water supply operation, and a suction button 131 for suction operation. In addition, the hand operation part 121 is provided with a still image capturing instruction unit 132 for giving an imaging instruction of a still image of a part to be observed and a treatment tool inlet 133 that allows a treatment tool (not illustrated) to be inserted into a treatment tool insertion passage (not illustrated) which is inserted in the insertion part 120.

The universal cord 122 is a connection cord for connecting the endoscope scope 102 to the light source device 111. The universal cord 122 includes a light guide 135 that is inserted in the insertion part 120, a signal cable 136, and a fluid tube (not illustrated). In addition, a connector 137*a* that is connected to the light source device 111 and a connector 137*b* that is branched from the connector 137*a* and is connected to the endoscope processor device 112 are provided at an end part of the universal cord 122.

By connecting the connector 137*a* to the light source device 111, the light guide 135 and the fluid tube (not illustrated) are inserted into the light source device 111. Accordingly, necessary illumination light, water, and a gas are supplied from the light source device 111 to the endoscope scope 102 via the light guide 135 and the fluid tube (not illustrated). As a result, illumination light is emitted from an illumination window (not illustrated) in the distal end surface of the distal end portion 127 toward a part to be observed. In addition, a gas or water is jetted from an air supply and water supply nozzle (not illustrated) on the distal end surface of the distal end portion 127 toward the observation window (not illustrated) in the distal end surface according to pressing operation of the air supply and water supply button 130 described above.

By connecting the connector 137*b* to the endoscope processor device 112, the signal cable 136 and the endoscope processor device 112 are electrically connected to each other. The signal cable 136 outputs an image pick-up signal of a part to be observed from the imaging element (not illustrated) of the endoscope scope 102 to the endoscope processor device 112, and outputs a control signal from the endoscope processor device 112 to the endoscope scope 102.

The light source device 111 supplies illumination light to the light guide 135 of the endoscope scope 102 via the connector 137*a*. As the illumination light, light in various types of wavelength ranges in line with an observation purpose, including white light (light in a white wavelength range or light in a plurality of wavelength ranges), light in one or a plurality of certain wavelength ranges, and light in a combination thereof, is selected. The certain wavelength range is a range narrower than the white wavelength range.

A first example of the certain wavelength range is, for example, a blue range or a green range in a visible light region. The wavelength range of the first example includes a wavelength range of 390 nm or more to 450 nm or less or 530 nm or more to 550 nm or less, and the light of the first example has a peak wavelength in a wavelength range of 390 nm or more to 450 nm or less or 530 nm or more to 550 nm or less.

A second example of the certain wavelength range is, for example, a red range in the visible light region. The wavelength range of the second example includes a wavelength range of 585 nm or more to 615 nm or less or 610 nm or more to 730 nm or less, and the light of the second example has a peak wavelength in a wavelength range of 585 nm or more to 615 nm or less or 610 nm or more to 730 nm or less.

A third example of the certain wavelength range includes a wavelength range in which a light absorption coefficient differs between oxyhemoglobin and reduced hemoglobin, and light of the third example has a peak wavelength in a wavelength range in which a light absorption coefficient differs between oxyhemoglobin and reduced hemoglobin. The wavelength range of the third example includes a wavelength range of 400±10 nm, 440±10 nm, 470±10 nm, or 600 nm or more to 750 nm or less, and the light of the third example has a peak wavelength in a wavelength range of 400±10 nm, 440±10 nm, 470±10 nm, or 600 nm or more to 750 nm or less.

A fourth example of the certain wavelength range is a wavelength range (390 nm to 470 nm) of excitation light that is used in observing fluorescence (fluorescence observation) emitted from a fluorescent substance in a body of a patient and excites the fluorescent sub stance.

A fifth example of the certain wavelength range is a wavelength range of infrared light. The wavelength range of the fifth example includes a wavelength range of 790 nm or more to 820 nm or less or 905 nm or more to 970 nm or less, and the light of the fifth example has a peak wavelength in a wavelength range of 790 nm or more to 820 nm or less or 905 nm or more to 970 nm or less.

The endoscope processor device 112 controls an operation of the endoscope scope 102 via the connector 137*b* and the signal cable 136. In addition, the endoscope processor device 112 generates a motion image that consists of a time-series frame image based on an image pick-up signal acquired from the imaging element (not illustrated) of the endoscope scope 102 via the connector 137*b* and the signal cable 136. A frame rate of the motion image is, for example, 30 frames per second (fps).

Further, in a case where the still image capturing instruction unit 132 is operated by the hand operation part 121 of the endoscope scope 102, the endoscope processor device 112 acquires one frame image of a motion image in parallel with the generation of a motion image according to a timing of imaging instruction, and sets the frame image as a still image.

Herein, the endoscope processor device 112 acquires the current date and time, a scope ID of the endoscope scope 102, information on a patient/examination, information on a facility where the endoscope system 100 is provided, and causes, along with the subject image 30, the date and time information 32, the scope ID 34, the patient/examination ID 36, and the facility information 38 (each refers to FIG. 2) to be imaged in each frame image and each still image of a motion image.

For example, the endoscope processor device 112 acquires the current time from a built-in clock function, and causes the current time to be imaged in a still image and a motion image as the date and time information 32. In addition, the endoscope processor device 112 acquires information on a patient/examination and information on a facility where the endoscope system 100 is provided from an input unit (not illustrated), and causes the information to be imaged in the still image and the motion image as the patient/examination ID 36 and the facility information 38. The scope ID 34 will be described later.

A motion image and a still image are endoscope images obtained by imaging an inside of a body of a patient. Further, in a case where the motion image and the still image are images obtained with light (special light) in the certain wavelength range, both images are special light images.

Based on feature amounts of pixels of a motion image and a still image, the endoscope processor device 112 may detect a region of interest that is a region which requires attention, or may detect the presence or absence of a target which requires attention.

In addition, the endoscope processor device 112 may generate (acquire) a special light image having information on the certain wavelength range based on a normal light image obtained from the white light. In this case, the endoscope processor device 112 functions as a special light image acquisition unit. Then, the endoscope processor device 112 obtains a signal in the certain wavelength range by performing calculation based on RGB color information such as red, green, and blue or CMY color information such as cyan, magenta, and yellow, which is included in the normal light image.

In addition, the endoscope processor device 112 may generate a feature amount image such as a known oxygen saturation image, for example, based on at least one of the normal light image obtained by the white light or the special light image obtained by the light (special light) in the certain wavelength range. In this case, the endoscope processor device 112 functions as a feature amount image generation unit. A motion image and a still image including the normal light image, the special light image, and the feature amount image are all endoscope images which are obtained through imaging results of imaging or measuring a human body for the purpose of diagnosis and examination based on an image.

The endoscope processor device 112 comprises the still image storage unit 20 (refer to FIG. 1). The endoscope processor device 112 stores a generated still image in the still image storage unit 20. The still image storage unit 20 may be connected to the endoscope processor device 112 so as to be capable of communicating in a wired or wireless manner, or may be an attachable and detachable recording medium.

The display device 113 is connected to the endoscope processor device 112. The endoscope processor device 112 outputs a generated motion image and a generated still image to the display device 113. The display device 113 displays the motion image and the still image which are input from the endoscope processor device 112. An endoscope operator performs forward and backward moving operation of the insertion part 120 while checking the motion image displayed on the display device 113. In addition, in a case where a lesion or the like is found in a part to be observed, the endoscope operator operates the still image capturing instruction unit 132 to capture a still image of the part to be observed and performs diagnosis and a biopsy.

The recording device 114 is connected to the endoscope processor device 112. The recording device 114 comprises the motion image storage unit 22 (refer to FIG. 1). The endoscope processor device 112 outputs a generated motion image to the recording device 114. The recording device 114 stores the motion image input from the endoscope processor device 112 in the motion image storage unit 22.

The endoscope system 100 may comprise an endoscope scope 104 which is an object different from the endoscope scope 102. A configuration of the endoscope scope 104 is the same as a configuration of the endoscope scope 102. The endoscope scope 104 can be used in the same manner as the endoscope scope 102 by connecting the connector 137a to the light source device 111 and connecting the connector 137b to the endoscope processor device 112. The endoscope scope 104 may be a scope having the same model number as the endoscope scope 102 or may be a scope having a different model number.

A unique scope ID is assigned to each of the endoscope scopes 102 and 104. The endoscope processor device 112 can acquire the scope IDs of the endoscope scopes, to which the connector 137b is connected, via the signal cable 136. The endoscope processor device 112 causes the acquired scope ID to be imaged in a still image and a motion image as the scope ID 34.

The endoscope processor device 112 may acquire a still image from the still image storage unit 20 and detects one or both of a region of interest that is a region which requires attention and is included in the still image and the presence or absence of a target which requires attention.

The endoscope processor device 112 may acquire a motion image from the motion image storage unit 22, and detect one or both of a region of interest that is a region which requires attention and is included in the motion image and the presence or absence of a target which requires attention.

The endoscope system 100 that functions as a medical image processing device may be provided in a diagnosis support device or a medical support device.

The filing device 10 associates a still image and a motion image, which are captured by the endoscope system 100 configured as described above, with each other. In the endoscope system 100, the still image is stored by the endoscope processor device 112, and the motion image is stored by the recording device 114. For this reason, it is difficult to match the still image and the motion image based on metadata, such as exchangeable image file format (Exif) information, in some cases. The filing device 10 can appropriately associate the still image with the motion image without using the metadata by analyzing pixel values of the still image and the motion image.

Although a still image and a motion image to be associated with each other have been described as examples of endoscope images herein, the still image and the motion image are not limited to the endoscope images.

Others

In the embodiments described hereinbefore, for example, a hardware structure of a processing unit, which executes various types of processing of the filing device 10 and the endoscope processor device 112, includes various types of processors as follows. The various types of processors include a central processing unit (CPU) that is a general-purpose processor which executes software (program) and functions as various types of processing units, a graphics processing unit (GPU) that is a processor specialized in image processing, and a dedicated electric circuit or the like that is a processor having a dedicated circuit configuration designed to execute certain processing, such as a programmable logic device (PLD) and an application specific integrated circuit (ASIC) which are processors of which a circuit configuration can be changed after manufacturing a field programmable gate array (FPGA) or the like.

One processing unit may be configured by one of the various types of processors, or may be configured by the same type or different types of two or more processors (for example, a plurality of FPGAs, a combination of a CPU and an FPGA, or a combination of a CPU and a GPU). In addition, a plurality of processing units may be configured by one processor. As an example of configuring a plurality of processing units by one processor, first, there is a form in which one processor is configured by a combination of one or more CPUs and software and the processor functions as the plurality of processing units, as represented by a computer such as a server and a client. Second, there is a form in which a processor that realizes functions of the entire system including a plurality of processing units with one integrated circuit (IC) chip is used, as represented by a system on chip (SoC) or the like. As described above, the various types of processing units are configured using one or more of the various types of processors as a hardware structure.

Further, the hardware structure of the various types of processors is, more specifically, an electric circuit (circuitry) in which circuit elements such as semiconductor elements are combined.

The technical scope of the present invention is not limited to the scope described in the embodiments. The configuration and the like in each embodiment can be combined between the embodiments as appropriate without departing from the gist of the present invention.

EXPLANATION OF REFERENCES

10: filing device
12: acquisition unit
14: still image analysis unit
16: motion image analysis unit
18: associating unit
20: still image storage unit
22: motion image storage unit
30: subject image
32: date and time information
34: scope ID
36: patient/examination ID
38: facility information
100: endoscope system
102: endoscope scope
104: endoscope scope
111: light source device
112: endoscope processor device
113: display device
114: recording device
120: insertion part
121: hand operation part
122: universal cord
125: flexible portion
126: curving portion
127: distal end portion
129: curving operation knob
130: air supply and water supply button
131: suction button
132: still image capturing instruction unit
133: treatment tool inlet
135: light guide
136: signal cable
137a: connector
137b: connector

What is claimed is:

1. A filing device comprising:
a storage that stores a plurality of still images and at least one motion image, wherein each of the still images is one of frame images obtained by imaging a patient with an endoscope system and captured from imaging starting date and time to imaging finishing date and time, the one of the frame images is acquired and stored between the imaging starting date and time and the imaging finishing date and time as the still image by an endoscope processor device
the at least one motion image is constituted of the frame images and stored between the imaging starting date and time and the imaging finishing date and time by a recording device connected to the endoscope processor device, wherein the plurality of still images are imprinted with still image information, and the at least motion image is imprinted with motion image information; and
a processor configured to:
acquire a still image group constituted of the still images stored in the storage within a certain period, from the storage, and acquire the at least one motion image from the storage;
analyze a pixel value of the still image group to extract the still image information including earliest imaging date and time and latest imaging date and time of the still image group;
analyze a pixel value of the at least one motion image to extract motion image information including imaging starting date and time and imaging finishing date and time of the at least one motion image;
compare the still image information with the motion image information; and
associate the still image group with the at least one motion image in a case where the earliest imaging date and time of the still image group are later than the imaging starting date and time of the at least one motion image and the latest imaging date and time of the still image group are earlier than the imaging finishing date and time of the at least one motion image.

2. The filing device according to claim 1, wherein the still image information and the motion image information include imaging date and time information.

3. The filing device according to claim 2, wherein the processor acquires a still image group, which is a group of a plurality of the still images stored within a certain period, from the first storage.

4. The filing device according to claim 3, wherein the processor associates a first motion image with a first still image group that is captured when the first motion image is captured.

5. The filing device according to claim 1, wherein the still image information and the motion image information include information on a scope of the endoscope system.

6. The filing device according to claim 1, wherein the still image information and the motion image information include information on the patient and an examination.

7. The filing device according to claim 1,
wherein the still image information and the motion image information include information on a facility where the endoscope images are captured.

8. A filing method comprising:
an acquiring step of acquiring a still image group constituted of a plurality of still images within a certain period and at least one motion image from a storage, wherein each of the still images is one of frame images obtained by imaging a patient with an endoscope system and captured from imaging starting date and time to imaging finishing date and time, the one of the frame images is acquired and stored between the imaging starting date and time and the imaging finishing date and time as the still image by an endoscope processor device, and the at least one motion image is constituted of the frame images and stored between the imaging starting date and time and the imaging finishing date and time by a recording device connected to the endoscope processor device, wherein the plurality of still images are imprinted with still image information, and the at least motion image is imprinted with motion image information;
a still image analyzing step of analyzing a pixel value of the still image group to extract the still image information including earliest imaging date and time and latest imaging date and time of the still image group;
a motion image analyzing step of analyzing a pixel value of the at least one motion image to extract motion image information including imaging starting date and time and imaging finishing date and time of the at least one motion image;
a comparison step of comparing the still image information with the motion image information; and
an associating step of associating the still image group with the at least one motion image in a case where the earliest imaging date and time of the still image group are later than the imaging starting date and time of the at least one motion image and the latest imaging date and time of the still image group are earlier than the imaging finishing date and time of the at least one motion image.

9. A non-transitory, tangible computer-readable medium which stores thereon computer instructions that, when read by a computer, causes the computer to execute a filing method comprising:
an acquiring step of acquiring a still image group constituted of a plurality of still images within a certain period and at least one motion image from a storage, wherein each of the still images is one of frame images obtained by imaging a patient with an endoscope system and captured from imaging starting date and time to imaging finishing date and time, the one of the frame images is acquired and stored between the imaging starting date and time and the imaging finishing date and time as the still image by an endoscope processor device, and the at least one motion image is constituted of the frame images and stored between the imaging starting date and time and the imaging finishing date and time by a recording device connected to the endoscope processor device, wherein the plurality of still images are imprinted with still image information, and the at least motion image is imprinted with motion image information;
a still image analyzing step of analyzing a pixel value of the still image group to extract the still image information including earliest imaging date and time and latest imaging date and time of the still image group;
a motion image analyzing step of analyzing a pixel value of the at least one motion image to extract the motion image information including imaging starting date and time and imaging finishing date and time of the at least one motion image;
a comparison step of comparing the still image information with the motion image information; and
an associating step of associating the still image group with the at least one motion image in a case where the earliest imaging date and time of the still image group are later than the imaging starting date and time of the at least one motion image and the latest imaging date and time of the still image group are earlier than the imaging finishing date and time of the at least one motion image.

* * * * *